(12) United States Patent
Albalat Estela

(10) Patent No.: US 11,000,228 B2
(45) Date of Patent: May 11, 2021

(54) INTRAORAL DEVICE

(71) Applicant: WITOOTH DENTAL SERVICES AND TECHNOLOGIES, S.L., Valencia (ES)

(72) Inventor: Salvador Albalat Estela, Valencia (ES)

(73) Assignee: WITOOTH DENTAL SERVICES AND TECHNOLOGIES, S.L., Valencia (ES)

( * ) Notice: Subject to any disclaimer, the term of this patent is extended or adjusted under 35 U.S.C. 154(b) by 0 days.

(21) Appl. No.: 15/741,477

(22) PCT Filed: Jul. 1, 2016

(86) PCT No.: PCT/ES2016/070494
§ 371 (c)(1),
(2) Date: Jan. 2, 2018

(87) PCT Pub. No.: WO2017/005952
PCT Pub. Date: Jan. 12, 2017

(65) Prior Publication Data
US 2018/0368767 A1 Dec. 27, 2018

(30) Foreign Application Priority Data
Jul. 3, 2015 (ES) ................................ P201530959

(51) Int. Cl.
A61B 5/00 (2006.01)
A61B 1/00 (2006.01)
A61B 5/053 (2021.01)
A61B 5/0205 (2006.01)
A61B 5/145 (2006.01)
G01N 33/49 (2006.01)

(52) U.S. Cl.
CPC ................ *A61B 5/682* (2013.01); *A61B 1/00* (2013.01); *A61B 5/0031* (2013.01); *A61B 5/0205* (2013.01); *A61B 5/053* (2013.01); *A61B 5/14532* (2013.01); *A61B 5/14542* (2013.01); *A61B 5/4362* (2013.01); *A61B 5/7225* (2013.01); *A61B 5/74* (2013.01); *G01N 33/49* (2013.01); *A61B 5/0015* (2013.01)

(58) Field of Classification Search
CPC .................................. A61B 5/682; A61B 1/00
See application file for complete search history.

(56) References Cited

U.S. PATENT DOCUMENTS

| 5,212,476 A | * | 5/1993 | Maloney | ............ | A61B 5/04886 340/4.11 |
| 2006/0025700 A1 | * | 2/2006 | Fallik | ....................... | A61B 5/01 600/537 |
| 2011/0301414 A1 | | 12/2011 | Hotto | | |

(Continued)

*Primary Examiner* — Hsinchun Liao
(74) *Attorney, Agent, or Firm* — Horst M. Kasper, Esq.

(57) ABSTRACT

The invention relates to an intraoral device (1) comprising: a programmable electronic microcircuit (2) with a series of ports, in each of which a microsensor can be connected; means for powering the electronic microcircuit (2); and means for the wireless communication of data from the device, all disposed inside a sealed, thermally insulated protective element (3). According to the invention, the protective element (3) is secured to the surface of, or inside a support element located inside the oral cavity, the dimensions of said protective element (3) being adapted to the dimensions of the support element.

17 Claims, 4 Drawing Sheets

(56) References Cited

U.S. PATENT DOCUMENTS

| | | | |
|---|---|---|---|
| 2012/0316486 A1* | 12/2012 | Cheung | A61C 1/082 602/48 |
| 2015/0045850 A1* | 2/2015 | Bork | A61N 1/0509 607/40 |
| 2015/0150501 A1* | 6/2015 | George | A61B 5/4833 600/301 |

* cited by examiner

INTRAORAL DEVICE

CROSS REFERENCE TO RELATED APPLICATIONS

This application claims priority to the following Patent Applications: (1) PCT application PCT/ES2016/070494, filed Jul. 1, 2016: and (2) Spanish Patent application P201530959 filed Jul. 3, 2015. The above-identified applications are hereby incorporated by reference in entirety as if fully set forth herein.

TECHNICAL FIELD OF THE INVENTION

This invention is classified within the technical field of medical devices of class III in the human body, in particular within the field of active medical devices for diagnosing and controlling multiple parameters and constants, as well as for the communication thereof.

BACKGROUND OF THE INVENTION

At present, the use of mobile communication devices is widespread and common.

On the one hand, these devices pose a problem in very cold areas of the planet where, due to the low temperatures, it is impossible to make a normal use of them, as hand protection must be worn. In the same sense, there are certain professions in which you cannot have your hands free due to being busy with other tasks, and there are also people with disabilities affecting their upper extremities, meaning that they are faced with the same problem when interacting with their mobiles.

On the other hand, the frequent use of mobile devices has resulted in them being developed and in them evolving, in turn allowing their use to be extended to different applications in the field of health; some of which allow different vital signs and physiological states to be parameterised. This technology allows multiple vital signs to be registered through various devices connected to a mobile, to which they send the obtained results and from which these devices can be managed.

In certain clinical cases, the continuous monitoring of a patient is necessary, such as in the case of blood glucose control in diabetics. The blood glucose rate of an insulin-dependent diabetic should be measured two to three times a day, and it is essential for the patient's health for this control to be performed accurately. State-of-the-art devices have been developed that aim to monitor parameters such as the example of glucose. These devices are usually invasive, requiring the insertion of a sensor in the subcutaneous tissue. These sensors are usually linked to a connector that is fixed to the user's skin by means of an adhesive and allow electronic signals from the sensor to be transmitted via a cable to the monitor.

This results in discomfort for the patient, both at the time in which the device is implanted, and in their everyday life, as having to wear the connector as an external element adhered to their skin on some part of their body can also be a nuisance, inconvenient in certain circumstances, especially at times when less clothing is won and the connector is highly visible.

There is a large amount of substances that need to be controlled, such as antigens, antibodies, cholesterol, neurochemical compounds, etc.

Reference documents ES-2186566-B1, ES-2278723-T3 and ES-2014649-A6 may be highlighted as an example of the state of the art.

Reference document ES-218656-B1 refers to an intravenous biosensor for measuring blood conductivity which, materialised in an invasive sensor for biochemical analysis, is constituted by two microelectrodes integrated into a hypodermic needle, with its end opposite the insertion tip topped in a flat sheet, preferably silicone, in order to be attached to the patient's skin, microelectrodes which, through conductors that are duly encapsulated in a sheath, are connected to an electronic measuring circuit provided with a display module.

This case is an example of the available stale-of-the-art devices, which are invasive sensors that are introduced into the dermal layer of the user and produce a foreign body in the patients body.

These devices are quite cumbersome and uncomfortable, both through their own invasive placement, and due to the fact that most of the time they require an external device to be connected to the sensor, which as has already been explained, is uncomfortable for the user and highly impractical.

Reference document ES-2278723-T3 refers to a hand-held portable device with a reusable biosensor, which is used in particular for the decentralised determination of original biological solutions. It comprises an amperometric biosensor, a measuring cell, a supply bag and a waste beg for a fresh and used system solution, a pump, a peristaltic transport system, a sample opening and a sample channel, a functional control with valve function and pump control, a lever for replacing the sensor, a display, four control elements, a 9V battery, a solar cell, an evaluation unit for recording signals and the overall control of the measurement process.

In this case, the biosensor has an advantage over other biosensors as it is portable, but it takes the measurement from previously extracted samples. It is therefore not valid for performing a continuous control of a given patient parameter, but it does take measurements from previously obtained samples.

Document ES-2014649-A6 refers to a biosensor-inserting device, comprising an arched needle, a biosensor secured in the arched needle behind its tip, and means for inserting the needle under the skin in order to insert the biosensor subcutaneously.

In this case, it is a device for inserting a low biosensor under the user's skin, which again shows the tendency to use invasive biosensors located in an inner layer of the skin, which are not comfortable or practical.

It can therefore be observed that all the currently available state-of-the-art sensors, or those used in monitoring—with the drawback of having to be inserted in an invasive and uncomfortable manner in the user's body and proving impractical in their day to day-, are either sensors that do not aim to monitor but simply obtain isolated values over time.

DESCRIPTION OF THE INVENTION

The intraoral device presented herein comprises a programmable electronic microcircuit with a series of ports with microsensor connections, means for feeding the electronic microcircuit and means for communicating the data from these wirelessly. AN these elements are included inside a watertight and thermally insulated element. This watertight element is attached to the surface or inside a support element within the buccal cavity, and its dimensions are adapted to the size of the support element.

In accordance with a preferred embodiment, the means for feeding the electronic microcircuit are formed by a micro battery.

In this case, according to a preferred embodiment, the micro battery is rechargeable and, according to another preferred embodiment, the micro battery is replaceable.

In accordance with another aspect, in a preferred embodiment, the intraoral device includes a biological microsensor in at least one connection port.

According to a preferred embodiment, it includes an acoustic microsensor formed by a microphone in at least one connection port.

In accordance with a preferred embodiment, it includes an acoustic microsensor formed by a speaker in at least one connection port.

According to another aspect, in a preferred embodiment, the wireless data communication means include a Wi-Fi communication antenna.

According to another preferred embodiment, said wireless data communication means include a Bluetooth communication antenna and in another preferred embodiment, they include a radio communication antenna.

In some embodiments, the communication means include an NFC communications module and an antenna connected to the NFC communications module.

In embodiments, the antenna and the NFC communications module define the power means so that the antenna receives radio frequency energy from an external power source and converts it into an output voltage using the NFC communications module so as to power the electronic microcircuit.

According to another aspect, which is also preferred, the support element is formed by a dental prosthesis. This preferred dental prosthesis is formed by a dental crown placed on an endosseous dental implant. In another preferred embodiment, it is formed by the intermediate part of a dental bridge and, according to another preferred embodiment, it is formed by a denture.

According to another preferred embodiment, the support element is formed by a endoaseous dental implant.

This proposed intraoral device boasts a significant improvement in terms of the level of the state of the art.

In other words, a device is obtained which is placed within a support element inside the oral cavity of the user, but which does not form part of the user's body. Taking into consideration that, at present, the vast majority of people have dental implants or bridges, this intraoral device takes advantage of these elements as a support for the device, and as they are elements that do not form part of the user's body, the implantation process does not generate pain or any discomfort.

It is a device in which different sensors can be connected in the various ports, thus offering multiple uses.

Through this, it is possible to connect biological sensors that allow the real-time recording and monitoring of vital and biochemical signs for monitoring and diagnosing diseases that require this, such as diabetes, cardiovascular diseases, hypertension etc. In these cases, the advantage offered by this device is that it enables registries to be made through communication with smartphone devices and through electronic applications developed for the same purpose.

Therefore, and as the communication with mobile devices is wireless—either via Wi-Fi, Bluetooth, NFC or radio—, the external connectors which must always be carried by the user permanently and which are normally attached to their body or attached through other means in the state of the art are not necessary.

Similarly, this device can carry a sound sensor formed by a microphone and/or speaker, which may be used by the user in order to be able to use a mobile phone without having to handle it directly with their hands in those locations where weather conditions complicate the possibility of handling them normally. It also represents a solution for professionals who need to access their mobile phones but have difficulties in doing so due to the task that they are performing, or for people with physical disabilities.

Furthermore, other options include being able to listen to music without the need for external devices, improving the hearing of people with hearing problems, etc.

Part of the elements of this device, such as the electronic microcircuit or microsensors may also be manufactured using photonic technology. This achieves lower energy consumption and also better miniaturises microelectronics.

Therefore, this intraoral device is a device with multiple functions which are achieved in a way that eliminates the problems and drawbacks that currently exist with other alternatives. Furthermore, it functions in a simple and effective way, and is also practical and comfortable for the user.

BRIEF DESCRIPTION OF THE DRAWINGS

With the aim of promoting a better understanding of the characteristics of the invention, in accordance with a preferred example of a practical embodiment of the same, a series of drawings are provided as an integral part of the description in which, for merely illustrative purposes, the following has been represented.

DETAILED DESCRIPTION OF A PREFERRED EMBODIMENT OF THE INVENTION

In view of the Figures provided, it can be observed how in a preferred embodiment of the invention, the intraoral device 1 proposed comprises a programmable electronic microcircuit 2 with a series of ports with microsensor connections, means for feeding the electronic microcircuit 2 and means for communicating the data from these wirelessly.

Figure 1:
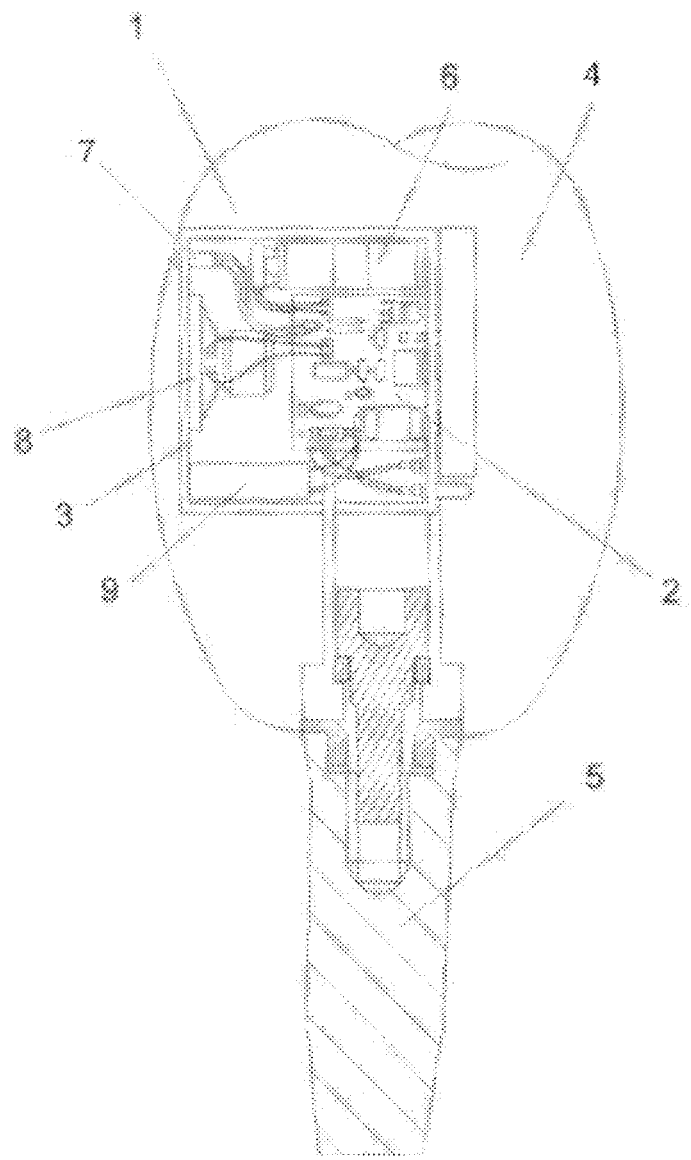
FIG. 1 shows a sectional view of an intraoral device placed in a support element for a preferred embodiment of the invention.

As shown in FIG. 1, said elements are all located inside a protective watertight and thermally insulated element 3. The protective element 3 on the other hand, is attached inside an internal support element within the oral cavity and its dimensions are adapted to the dimensions of this support element.

In this preferred embodiment of the invention, as can be seen in FIG. 1, the support element is formed by a dental prosthesis, specifically by a dental crown 4 placed on an endosseous dental implant 5, in such a way that the intraoral device 1 is held inside the crown 4 of said dental implant 5.

In some of the other examples, the device may be placed in the oral tissue, for example, in the gum or in the mucosa. In some of the other examples, the device may be placed below the gum or the mucosa, for example. The device may be placed under the gum or mucosa with a simple surgical procedure.

In this preferred embodiment of the invention, the means for feeding the electronic microcircuit 2 are formed by a micro battery 6, which in this case is a rechargeable micro battery.

In this preferred embodiment, the micro battery 6 is recharged via the use of a splint made for such purpose. In this way, the user can charge the micro battery 6 at night, placing the splint on the crown 4 with the intraoral device 1.

In this preferred embodiment of the invention, the intraoral device 1 comprises a biological microsensor 9 connected to a port in the intraoral device 1, for measuring the user's vital constants and, as shown in FIG. 1, it also comprises an acoustic microsensor formed by a microphone 7 and a second acoustic microsensor formed by a speaker 8.

The biological microsensor 9 can measure the following physiological parameters:

Heart rate: Information on the number of heart contractions per unit of time is of great importance, as it is a primary indicator for knowing the state of cardiovascular health of the user. Therefore, it allows any anomalies to be detected for the user. Specifically, in order to measure the heart rate, the biological microsensor 9 could be an infrared device configured to detect blood flow in the gum area.

Blood pressure: It is also a key parameter for detecting certain diseases e.g. cerebrovascular diseases. Specifically, the sensor 9 used could also be an infrared device configured to detect blood pressure in the gum area. In some examples, this sensor could measure the pressure and obtain a percentage of the pressure above or below the reference pressure.

Glucose: Various studies that show that hyperglycaemia is one of the most frequent complications in certain diseases. In this sense, during the development of certain diseases e.g. cerebrovascular diseases, users with hyperglycaemia seem to have a worse evolution.

Oxygen in blood: The cells of a person suffering from a disease, such as cardiovascular diseases, may die due to a lack of blood supply, meaning that the nerve cells are not receiving enough oxygen and have stopped working. For this reason, the comprehensive assessment of a patient's blood oxygen level is of vital importance. In this example, information on the blood oxygen levels can be extracted from the information obtained by the biological microsensor 9 in relation to the heart rate.

The wireless data communication means of the intraoral device 1 of this preferred embodiment of the invention include a Wi-Fi communication antenna.

In some of the examples, the communication means may also include an NFC communications module, as will be described in more detail based on FIGS. 2-5.

This proposed intraoral device boasts a significant improvement with respect to the state of the art.

In this sense, a device is obtained which is placed within a support element inside the oral cavity of the user and therefore, there is no need to perform any invasive placement procedures. Overall, this is much more comfortable for the user, and it also transfers all the data obtained through a wireless communication to a mobile device. In this way, there is no need for the user to depend on an invasive device with an external connector, which would be continually attached to the body.

Furthermore, the device boasts multiple functions which improve the monitoring conditions of the patients, as it monitors all the vital constants or parameters previously determined by the medical staff without the patients noticing.

Similarly, it can improve the living conditions of people with disabilities or hearing problems, and help by making the use of a mobile device possible in situations when the user cannot use their hands as they would usually, and it can even be used for leisure purposes to listen to music, amongst other uses.

It is therefore a very versatile device and at the same time practical and comfortable for the user, and really effective for carrying out the functions for which it has been programmed.

Figure 2:
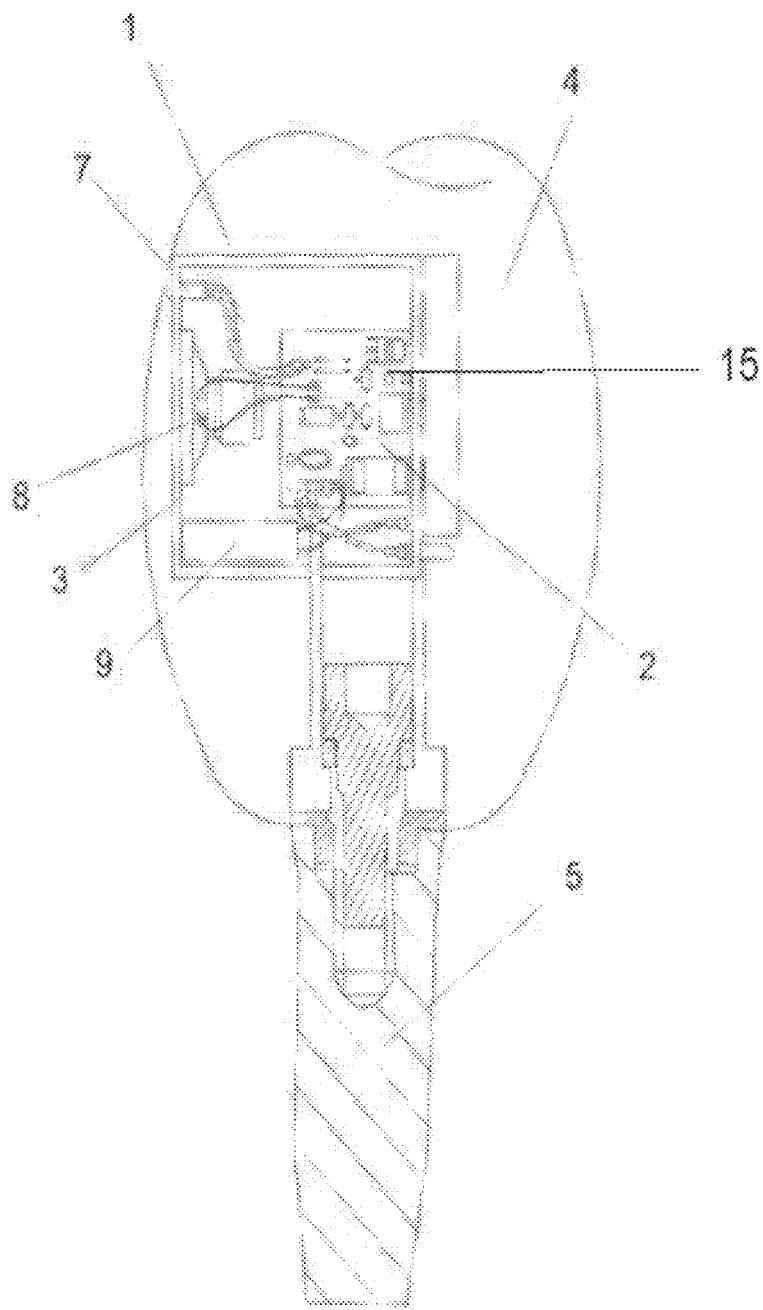
FIG. 2 shows a section of the intraoral device in another embodiment of the invention.

FIG. 2 shows a section of an intraoral device in another embodiment of the invention. The same reference numbers denote the same elements described in FIG. 1.

In FIG. 2 an embodiment is shown in which the intraoral device 1 does not include a battery. Instead, the collection of energy by a NFC communications module 15 15 and an antenna (not shown) coupled to the communications module 15 may be an appropriate form to supply power to the electronic microcircuit 2. Specifically, the antenna can be used as a feeding means, in such a way that it captures radio frequency (RF) energy, in other words, radiofrequency waves from the means and converts them into a supply voltage, for example, or a direct current using the NFC communications module 15.

NFC (Near Field Communication) technology is a wireless, short-range technology with a high frequency that allows the exchange of data between devices. NFC may require a separation of 10 cm or less between devices. In addition, NFC operates at 13.56 MHz according to ISO/IEC 18000-3 and at rates ranging from 106 kbit/s to 424 kbit/s.

As mentioned above, biological microsensors 9 can report information on the physiological parameters of a user, in real time and instantaneously, from the location of the intraoral device 1. As can be observed in FIG. 1, batteries can be a good solution for low consumption and periodic use applications, but they need to be continuously recharged. In addition, they require a high level of maintenance as they need to be replaced with others when their life cycle has passed.

As an alternative to batteries, it has been found that the use of an NFC module 15 and an antenna (not shown) as an energy harvesting system may be able to improve the autonomy of the system and increase its benefits (reducing the size and quantity of batteries needed, etc.). In addition, in the case of critical physiological parameter monitoring, the possibility of the batteries needing to be replaced without prior notice may exclude their use in a non-redundant manner.

In the example shown in FIG. 2, energy harvesting may be implemented by the NFC communications module 15 comprised in an intraoral device 1, where the NFC communications module 15 in turn comprises an antenna (not shown). Said NFC communications 15 module and antenna will be described in more detail based on FIGS. 3-5. In this way, the need for a battery can be eliminated.

Specifically, the NFC communications module 15 may comprise an RF module configured to receive radio waves, for example, by an RFID reader device or an NFC mobile telephone (not shown) using its antenna and converting those waves into an output voltage, which may be used to power the electronic microcircuit 2. Consequently, once the electronic microcircuit 2 is powered, the user can read the information, for example information collected by the biological microsensor 9, or write in the NFC 15 module.

In some of the examples, the energy collected by the NFC communications module 15 and the antenna can be stored in capacitors, super-capacitors or batteries, for example. In this way, the energy can be used at the most appropriate time.

Figure 3:
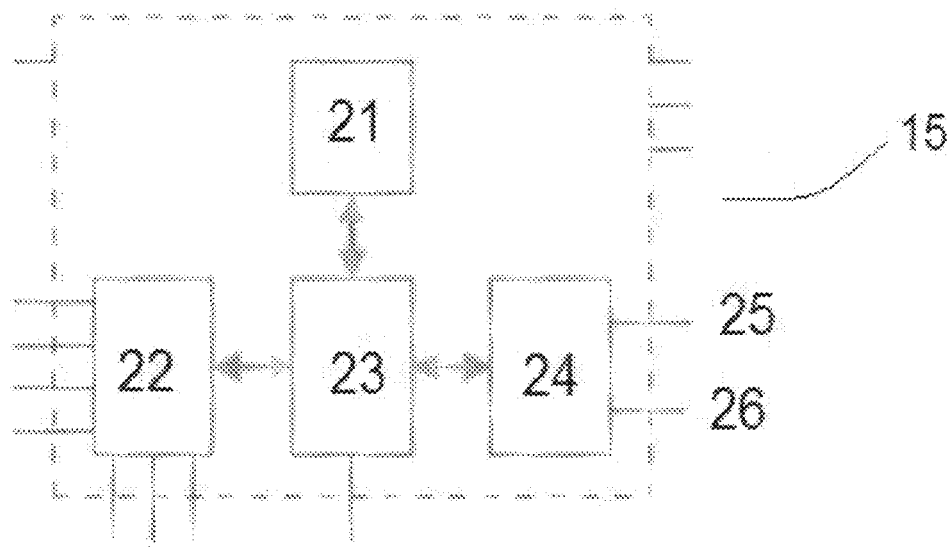
FIG. 3 shows a block diagram representing an NFC communications module according to some examples.

FIG. 3 shows a block diagram representing the different blocks or modules comprised in an NFC communications module 15, used for example in the intraoral device shown in FIG. 2.

In this way, FIG. 3 shows a block 21 that could represent a storage module. Said module 21 may comprise one or more memories for storing elements such as physiological parameters related to a user, including input signals from the sensors 9. For example, block 21 may comprise a SRAM (Static Random Access Memory) family memory configured to be written using either module 22 or 24. In addition, block 21 can also be read through modules 22 or 24. The structure and operation of the modules 22 and 24 will be described in detail below.

Specifically, block 22 could represent an I2C/SPI interface (Inter Integrated Circuit Communications (I2C) or a Serial-Peripheral Interface (SPI)). The SPI interface is a communications standard, used mainly for transferring information between integrated circuits in electronic equipment. The SPI bus or serial peripheral interface bus is a standard for controlling almost any digital electronic device that accepts a serial bit stream regulated by a clock (synchronous communication). In relation to the I2C interface, it is mainly used internally for communication between different parts of a circuit, for example, between a controller and integrated peripheral circuits.

The block 23 could represent a processing unit, for example, a microprocessor. The processing block 23 can be configured to process and analyse the information obtained through the input/output blocks 22 or 24. Said processing block 23 can integrate numerous peripherals e.g. analogue/digital conversion, communications with series/parallel buses, memories, PWM modules, communications. In this way, due to the high level of integration, the instructions related to the different functionalities of the processing unit 23 can be executed at high speed. The order of priorities between different tasks can also be determined. The processing block 23 can also simultaneously, quickly and efficiently respond to the input signals obtained by the blocks 22 or 24.

Block 24 could represent an RF interface. Specifically, the block 24 is based on the specification ISO14443B. This block 24 can support transmission rates of 106, 212, 424 and 848 Kbps, for example. Block 24 may further comprise a first and a second connection pins 25, 26 configured to be connected to the external antenna (not shown). The parameters and dimensions of the antenna may depend on, for example, the communication distance, the available space, etc.

Furthermore, as will be explained in more detail below with reference to FIG. 4, block 24 may comprise an integrated resonance capacitor (not shown). The capacitor may have, for example, a value of 35 pF with a tolerance of ±10%.

A resonance circuit may be generated using the external antenna (not shown) and an integrated internal resonance capacitor. In some of the examples, the NFC communication system 15 may also comprise an external capacitor (not shown) in order to slow variations in the inductance of the antenna in the case of low inductance antennas. The resonance frequency can be calculated using the equation:

$$fres = \frac{1}{2*\pi*\sqrt{L*C}}$$

In said equation, C refers to the resonance of the capacitor. In some of the examples, the resonance of the capacitor may be the sum of the value of the capacitance in the internal resonance capacitor and the capacitance value in the external capacitor. In addition, L refers to the inductance of the antenna and fres to the resonance frequency.

Taking into account the system described above, an example of the functioning of the NFC communications system 15 can be described as follows. The block 21 can be accessed through the block 22 in such a way that information related to the input signals in the sensors 9 can be written and/or read in block 21. In addition, block 21 can also be accessed via wireless connection through block 24.

Additionally, as discussed with reference to FIG. 2, the antenna (not shown) connected to pins 25 and 26 can receive radio frequency waves and transform these waves into direct current through the NFC communications module 15, which makes it possible to power the electronic microcircuit 2.

Figure 4:
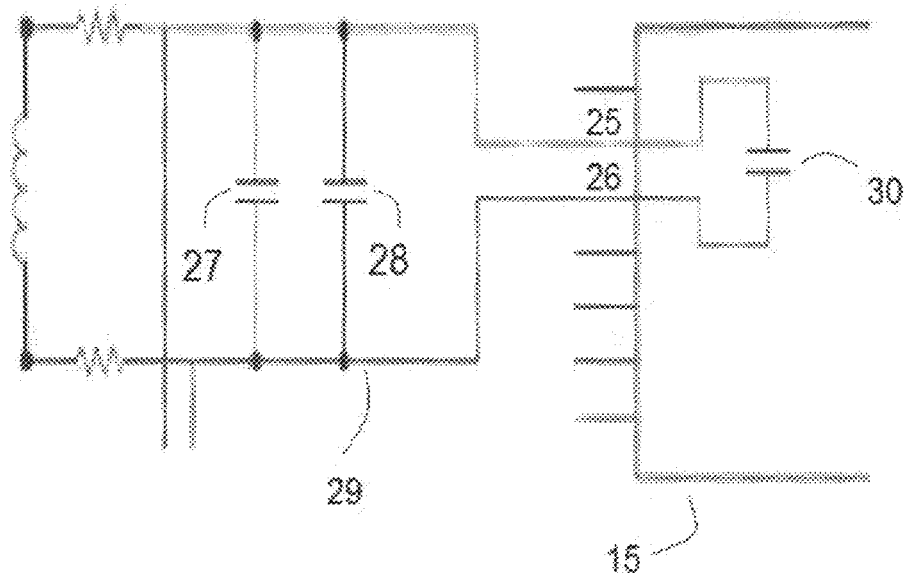
FIG. 4 shows an input circuit for the NFC communications module shown in FIG. 3, according to some examples.

FIG. 4 shows an input circuit for the NFC communications module 15 shown in FIGS. 2 and 3, according to some examples. Specifically, FIG. 4 shows an input circuit for the NFC RF430CL330H communications module.

The element 29 represents an external antenna 29. The elements 25 and 26 represent connection pins. This external antenna 29 can be connected to the NFC communications module via pins 25 and 26. The external antenna 29 may further comprise an internal capacitor 30. The antenna 29 together with an internal capacitor 30 can create a resonance frequency.

In some of the examples, the system may not comprise an external resonance capacitor. In this case, the resonance capacitor can only be the resonance of the internal capacitor 30, e.g. 35 pF.

In this specific example and depending on the inductance of the antenna 29, a first and a second external capacitors 27, 28 connected in parallel can be included in the antenna 29. In this example, the sum of the capacitances in parallel, that is, the sum of the capacitors 27, 28 and 30, is the value of the total capacitance.

During the development phase, it may be advisable to use an external adjustable capacitor to make a fine adjustment. This helps eliminate the tolerance component and the parasitic capacitance. During the production phase, the value of the adjustable capacitor can be measured and replaced by the external capacitors 27, 28, for example.

The recommended frequency of operation (fres) can typically be 13.7 MHz, with the aim of achieving the optimal functioning of the system. It has been found that resonance frequencies greater than 13.7 MHz lead to a reduction in system performance.

Once again, as previously mentioned, the antenna 29 can be responsible for capturing the radio frequency energy of, for example, a NFC mobile phone, while the NFC communications module 15 is responsible for converting the radio frequency energy captured by the antenna 28 to current acting antenna and NFC communications module, as means of powering the electronic microcircuit 2.

Figure 5:
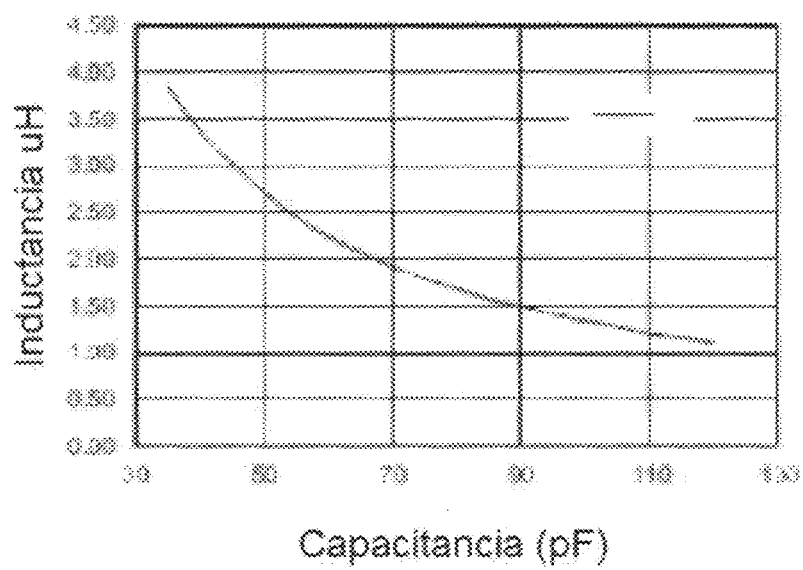
FIG. 5 shows a graphical representation with values of inductance and capacitance for generating resonance at 13.7 MHz in an embodiment of the invention.

FIG. 5 is a graph with values of inductance and capacitance for generating resonance at 13.7 MHz in an embodiment of the invention.

The Q factor, also called the quality or selectivity factor, is a parameter that measures the relationship between the reactive energy that can be stored and the energy that can be dissipated during a complete cycle of the signal. A high Q factor indicates a low rate of energy loss relative to the energy stored by the resonator.

The Q factor is an important parameter for oscillators, filters and other tuned circuits, as it provides a measure of how acute its resonance is.

The resonant systems respond to a certain frequency, called natural frequency, own frequency or frequency of resonance, at a much higher degree than to other frequencies. The bandwidth is the range of frequencies at which the system responds significantly, and the centre frequency is the frequency of the electrical resonance.

Typically, the passive quality factor (Q) in the circuit shown in FIG. 4 must be less than 50 pF. However, in some of the examples, the passive quality factor may be greater than 50 pF. In the case of passive quality factors (Q) greater than 50 pF, an external resistance (not shown) parallel to the capacitors 27, 28 shown in FIG. 4 may be provided. The value of the external resistance could be in the range between 10K Ω and 20K Ω.

Although only a few embodiments and particular examples of the invention have been described here, experts in the topic will understand that other alternative embodiments and/or uses of the invention are possible, as well as obvious modifications and equivalent elements. In addition, the present invention encompasses all possible combinations of the specific embodiments that have been described. The scope of the present invention should not be limited to specific embodiments, but should be determined solely by an appropriate reading of the attached claims

The invention claimed is:

1. An intraoral device (1), wherein the device comprises one or more microsensors,
   a programmable electronic microcircuit (2) with a series of ports connecting microsensors, and in at least one of the series of ports connecting microsensors a physiological parameter microsensor (9),
   means for feeding the electronic microcircuit (2) and
   wireless means for communicating any data of the same, all these elements being included inside a watertight and thermally insulated element (3), wherein the watertight and thermally insulated element is attached to a surface or inside a support element within a buccal cavity, wherein
   the watertight and thermally insulated element (3) is adapted to the support element.

2. The device according to claim 1, wherein the device comprises, in at least one of the series of ports connecting microsensors, a physiological parameter microsensor (9).

3. The device according to claim 2, wherein the device comprises, in at least one of the series of ports connecting microsensors, an acoustic microsensor in the form of a microphone (7).

4. The device according to claim 3, wherein the device comprises, in at least one of the series of ports connecting microsensors, a microsensor in the form of a speaker (8).

5. The device according to claim 1, wherein the element is formed by a dental prosthesis.

6. The device according to claim 5, wherein the dental prosthesis is formed by the intermediate part of a dental bridge.

7. The device according to claim 5, wherein the dental prosthesis is formed by a denture.

8. The device according to claim 1, wherein the dental prosthesis is formed by a dental crown placed on an endosseous dental implant.

9. The device according to claim 1, wherein the support element is formed by an endosseous dental implant.

10. The device according to claim 1, wherein the communication means comprises an NFC communications module and an antenna connected to the NFC communications module.

11. The device according to claim 10, wherein the antenna and the NFC communications module define the power supplying means, in such a way that the antenna receives radio frequency power from and external power source and the NFC communications module converts the power received by the antenna into output voltage in such a way that the microcircuit is powered.

12. The device according to claim 1, wherein the wireless data communication means comprises a Bluetooth communications antenna.

13. The device according to claim 1, wherein the power supplying means for the electronic microcircuit (2) is formed by a micro-battery (6).

14. The device according to claim 13, wherein the micro-battery (6) is rechargeable.

15. The device according to claim 13, wherein the micro-battery (6) is replaceable.

16. An intraoral device, wherein the device comprises one or more microsensors,
   a programmable electronic microcircuit with a series of ports connecting microsensors, and in at least one of the series of ports connecting microsensors, a physiological parameter microsensor, means for feeding the electronic microcircuit and
   wireless means for communicating any data of the same, all these elements being included inside a watertight and thermally insulated element, wherein the watertight and thermally insulated element is attached to a surface or inside a support element within a buccal cavity, wherein
   the watertight and thermally insulated element is adapted to the support element, and wherein,
wireless data communication means comprises a wi-fi communications antenna.

17. The device according to claim 16, wherein the wireless data communication means comprises a radio communications antenna.

* * * * *